(12) United States Patent
Matar et al.

(10) Patent No.: US 12,175,885 B1
(45) Date of Patent: Dec. 24, 2024

(54) 3D PRINTED HEART MODEL WITH SIMULATED CARDIAC STROKE VOLUMES

(71) Applicant: University of South Florida, Tampa, FL (US)

(72) Inventors: Fadi Matar, Tampa, FL (US); Jonathan Michael Ford, Apollo Beach, FL (US); Summer Joy Decker, Apollo Beach, FL (US)

(73) Assignee: UNIVERSITY OF SOUTH FLORIDA, Tampa, FL (US)

( * ) Notice: Subject to any disclaimer, the term of this patent is extended or adjusted under 35 U.S.C. 154(b) by 789 days.

(21) Appl. No.: 17/365,600

(22) Filed: Jul. 1, 2021

Related U.S. Application Data

(60) Provisional application No. 63/049,869, filed on Jul. 9, 2020.

(51) Int. Cl.

| | | |
|---|---|---|
| *G09B 23/30* | (2006.01) | |
| *B29C 64/393* | (2017.01) | |
| *B33Y 50/02* | (2015.01) | |
| *B33Y 80/00* | (2015.01) | |
| *G09B 23/32* | (2006.01) | |
| *G16H 30/40* | (2018.01) | |
| *A61B 5/026* | (2006.01) | |
| *A61B 6/50* | (2024.01) | |

(Continued)

(52) U.S. Cl.
CPC .......... *G09B 23/303* (2013.01); *B29C 64/393* (2017.08); *B33Y 50/02* (2014.12); *B33Y 80/00* (2014.12); *G09B 23/32* (2013.01); *G16H 30/40* (2018.01); *A61B 5/0263* (2013.01); *A61B 6/507* (2013.01); *A61B 8/065* (2013.01); *B29L 2031/40* (2013.01)

(58) Field of Classification Search
CPC ....... G09B 23/28; G09B 23/30; G09B 23/303
See application file for complete search history.

(56) References Cited

U.S. PATENT DOCUMENTS

| | | |
|---|---|---|
| 8,157,742 B2 | 4/2012 | Taylor |
| 8,682,626 B2 | 3/2014 | Ionasec et al. |

(Continued)

OTHER PUBLICATIONS

Mihalef et al., "Patient-specific modeling of left heart anatomy, dynamics and hemodynamics from high resolution 4D CT," 2010 IEEE International Symposium on Biomedical Imaging: From Nano to Macro, 2010, pp. 504-507.

*Primary Examiner* — Kurt Fernstrom
(74) *Attorney, Agent, or Firm* — Quarles & Brady LLP

(57) ABSTRACT

Disclosed herein is a 3D printed heart model with simulated cardiac stroke volumes. It involves an inner membrane conforming to the shape of the inner lining of the ventricle. This results in the creation of a compression pouch with a potential space (compression sac) bordered by the inner surface of the simulated ventricle and the outer surface of the inner membrane. The inner membrane also defines a neo-ventricular chamber that is in contact with blood simulating fluid. A pulsatile flow pump can serve as a hydrodynamic driver for inflow and outflow into and out of the compression sac. This can exert a concentric force that compresses the inner sac and displaces the simulated blood residing in the neo ventricular cavity simulating systole. The fluid can then return back from the compression sac to the pump allowing the neo-ventricle to distend to accommodate returning simulated blood from the atrium simulating diastole.

18 Claims, 5 Drawing Sheets

(51) Int. Cl.
    *A61B 8/06*     (2006.01)
    *B29L 31/40*    (2006.01)

(56) References Cited

U.S. PATENT DOCUMENTS

| | | | |
|---|---|---|---|
| 9,129,053 B2 | 9/2015 | Mansi et al. | |
| 9,135,381 B2 | 9/2015 | Singer | |
| 9,405,996 B2 * | 8/2016 | Ionasec | G06T 13/20 |
| 11,087,641 B1 * | 8/2021 | Khachatryan | G09B 23/303 |
| 11,096,744 B2 * | 8/2021 | Oashi Torres Ayres | G06T 17/00 |
| 11,450,237 B2 * | 9/2022 | Grant | G09B 23/30 |
| 2011/0291321 A1 * | 12/2011 | Chan | B29C 33/3857 |
| | | | 264/222 |
| 2012/0034587 A1 * | 2/2012 | Toly | G09B 23/30 |
| | | | 434/267 |
| 2012/0089238 A1 * | 4/2012 | Kang | A61L 27/26 |
| | | | 623/23.72 |
| 2015/0250934 A1 * | 9/2015 | Min | A61M 60/427 |
| | | | 700/119 |
| 2021/0350723 A1 * | 11/2021 | Pirlot | G09B 23/285 |

* cited by examiner

3D PRINTED HEART MODEL WITH SIMULATED CARDIAC STROKE VOLUMES

CROSS-REFERENCE TO RELATED APPLICATIONS

This application claims benefit of U.S. Provisional Application No. 63/049,869, filed Jul. 9, 2020, which is hereby incorporated herein by reference in its entirety.

BACKGROUND

Three-dimensional (3D) printing is at the crossroads of printer and materials engineering, noninvasive diagnostic imaging, computer-aided design, and structural heart intervention. Cardiovascular applications of this technology development include the use of patient-specific 3D models for medical teaching, exploration of valve and vessel function, surgical and catheter-based procedural planning, and early work in designing and refining the latest innovations in percutaneous structural devices. In this review, we discuss the methods and materials being used for 3D printing today. However, a limitation of these models is that the simulated ventricles are static. Fluid simulating blood can be directionally pushed through this static model but this does not take into account the changes in ventricular volumes seen in systole and diastole. The valvular apparatus, papillary muscles, chordae tendineae that control the mitral valve are affected by the changes in ventricular geometry.

SUMMARY

Disclosed herein is a simulation of ventricular contractility in a 3D printed heart model while attached to a fluid-filled pulsatile flow loop system.

It some embodiments, the heart model involves a systolic delimiting cage (e.g. 3D printed as a net or cage) inserted into the neo-ventricular lumen of the printed anatomical model designed to conform to the surface of the ventricle in systole. The heart model can then also involve an elastic compression sac positioned between the systolic delimiting cage and the ventricular wall of the printed anatomical model, wherein the elastic compression sac is in fluid communication with a pulsatile pump and wherein the systolic delimiting cage defines a boundary for inflation of the elastic compression sac corresponding to the systolic ventricular volume.

It some embodiments, the heart model involves an inner membrane conforming to the shape of the inner lining of the ventricle. The simulated ventricle and the compressible inner membrane can be derived from 3D rendered images taken from the patient's heart. During the printing process, the inner membrane rim remains attached to the simulated ventricle and to the papillary muscle bases. This results in the creation of a compression pouch with a potential space (compression sac) bordered by the inner surface of the simulated ventricle and the outer surface of the inner membrane. The inner surface of the inner membrane will become the neo-ventricular chamber that is in contact with blood simulating fluid.

In either embodiments, the apex of the simulated ventricle can have an opening to which an external tube is attached in continuity with the compression sac. A pulsatile flow pump, connected through external tubes and valves, can serve as a hydrodynamic driver for inflow and outflow into and out of the compression sac. It can push a solution through a tubing system to distend the compression sac. This can exert a concentric force that compresses the inner sac and displaces the simulated blood residing in the neo ventricular cavity through the aortic valve simulating systole. The fluid can then return back from the compression sac to the pump via a return tube and another one-way valve and the compression sac expands. The neo-ventricle can then distend to accommodate returning simulated blood from the atrium simulating diastole.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
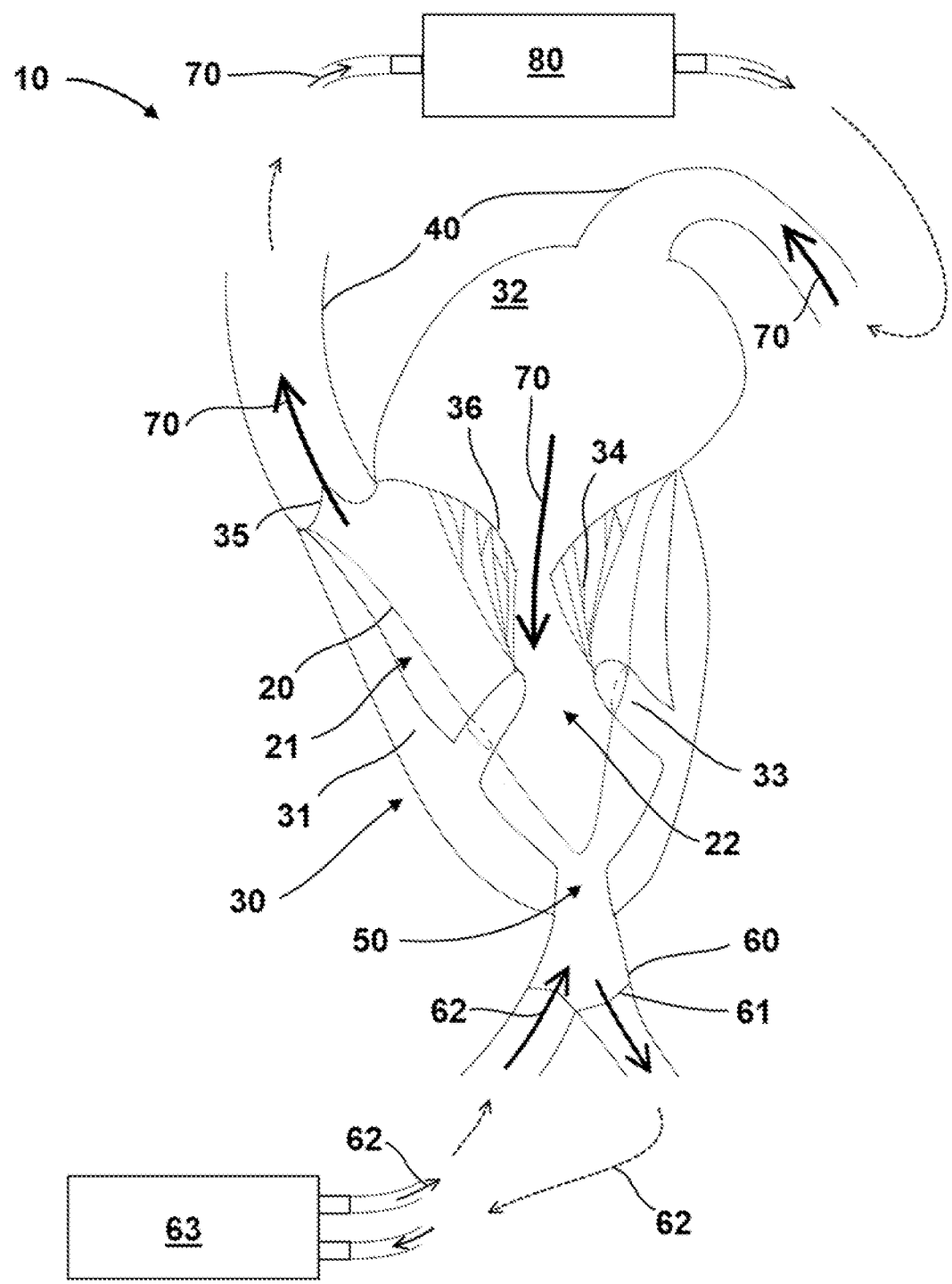
FIG. 1 illustrates an example embodiment of a disclosed 3D printed heart model with simulated cardiac stroke volumes.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of chemistry, biology, and the like, which are within the skill of the art.

The following examples are put forth so as to provide those of ordinary skill in the art with a complete disclosure and description of how to perform the methods and use the probes disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise.

Referring now to FIG. 1, shown is a partial left view of a 3D printed heart model 10 produced from an image of a subject's heart. The heart model 10 has a frame 30 mimicking the patient's heart anatomy, including a ventricular wall 31, atrium 32, papillary muscles 33, and chordae tendinae 34. The heart model 10 also contains an inserted or 3D printed elastic inner membrane 20 attached at fixation points to the frame 30, such as the papillary muscles 33, in order to define a compression sac 21 between the inner membrane 20 and simulated ventricular wall 31, and a new-ventricular lumen 22. The heart model 10 also contains a portal 50, e.g. positioned in the ventricular apex. that is in fluid communication with the compression sac 21. The portal 50 can be connected to a pulsatile pump 63 by hose(s) 60 configured to carry pulsatile flow 62 from and towards the pulsatile pump 63. In some cases, two hoses 60 are used that each contain a one-way valve 61 configured to divert pulsatile flow 62 in the correct direction.

In some embodiments, the heart model 10 also contains 3D printed valves, such as an aortic valve 35 and a mitral valve 36. In other embodiments, natural or synthetic valves are implanted in the heart model 10 after it is printed.

The heart model 10 can also contain a simulated aorta/vein complex 40 extending from the neo-ventricular lumen 22 to the simulated atria 32 filled with blood or a blood substitute to simulate blood flow 70. In order to simulate vascular resistance, i.e. to simulate physiological parameters, such as blood pressure, the heart model 10 can be attached to a flow resistor 80 that is configurable based on the subject's parameters.

Figure 2:
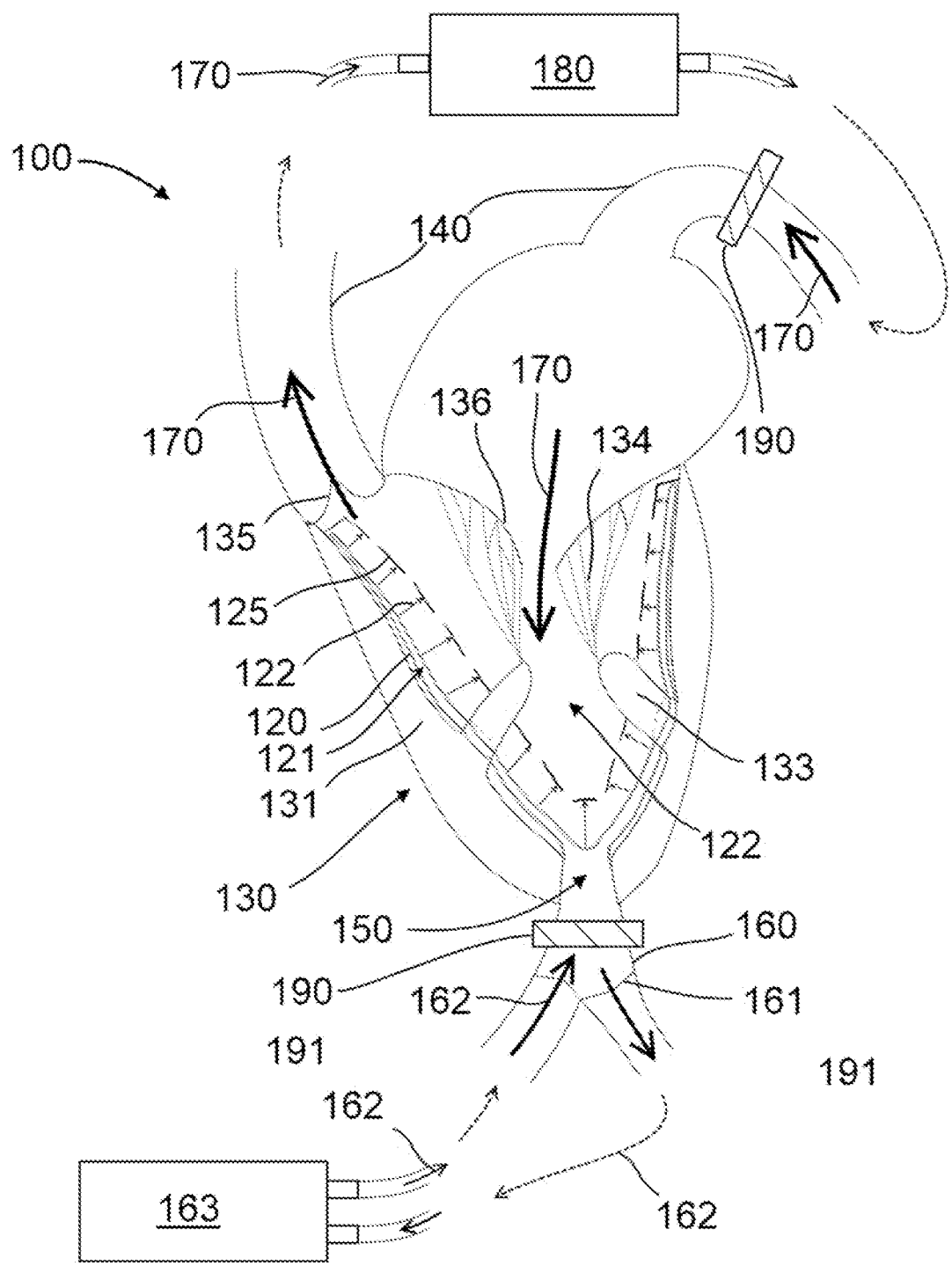
FIG. 2 illustrates an example embodiment of a disclosed 3D printed heart model with simulated cardiac stroke volumes.

Referring now to FIG. 2, shown is a partial left view of an alternative embodiment of a 3D printed heart model 100 produced from an image of a subject's heart. In this embodiment, the heart model 100 contains an inserted or 3D printed compression sac 120 between the simulated ventricular wall 131 and a systolic delimiting cage 125. The compression sac 120 has a lumen 121 that when filled causes the compression sac 120 to inflate in the direction 122 of the delimiting cage 125. The delimiting cage 125 is printed using a rigid material and therefore defines a boundary for inflation of the compression sac 120. The compression sac has portal 150, e.g. positioned in the ventricular apex that is in fluid communication with the compression sac 120. The portal 150 can be connected to a pulsatile pump 163 by hose(s) 160 configured to carry pulsatile flow 162 from and towards the pulsatile pump 163. In some cases, two hoses 160 are used that each contain a one-way valve 161 configured to divert pulsatile flow 162 in the correct direction. The heart model 100 can also contain a simulated aorta/vein complex 140 extending from the neo-ventricular lumen 122 to the simulated atria 132 filled with blood or a blood substitute to simulate blood flow 170. In order to simulate vascular resistance, i.e. to simulate physiological parameters, such as blood pressure, the heart model 100 can be attached to a flow resistor 180 that is configurable based on the subject's parameters. The heart model 100 can also contain adaptors 190 to connect the heart model 100 to the hoses 160. In some embodiments, the heart model 100 also contains 3D printed valves, such as an aortic valve 135 and a mitral valve 136. In other embodiments, natural or synthetic valves are implanted in the heart model 100 after it is printed.

In some embodiments, the 3D printed heart model is printed as separate pieces that are assembled together. For example, in some embodiments, the cardiac outer shell is printed first. The compression sac is printed and then placed into the cardiac outer shell using the mitral annulus opening. The nozzle of the compression sac is placed through the apex inlet. The systolic delimiting cage is advanced through the annular opening and the groove of base fitted into the tongue of at the base of the outer shell underneath the annular plane. The atrium and valvular apparatus are printed and advanced the atrial annulus opening. The bases of the papillary muscles are fitted in the indentations within the ventricular cavity. In some embodiments, they are affixed to them using adhesive and screws inserted from the outside of the cardiac shell. In the case of models with prosthetic valves without papillary muscles, cords and valves, then this step is not necessary. The compression sac nozzle is attached to Y-tubes via an adaptor. The tubings connect to a pulsatile flow pump with one-way valves. This allows for fluid to pressurize the compression sac causing sac compression followed by suction of the fluid back to the pump and sac collapse simulating diastole. The Aorta or pulmonary artery is connected via adaptors to the atrial return to complete a closed flow loop.

Figure 3:
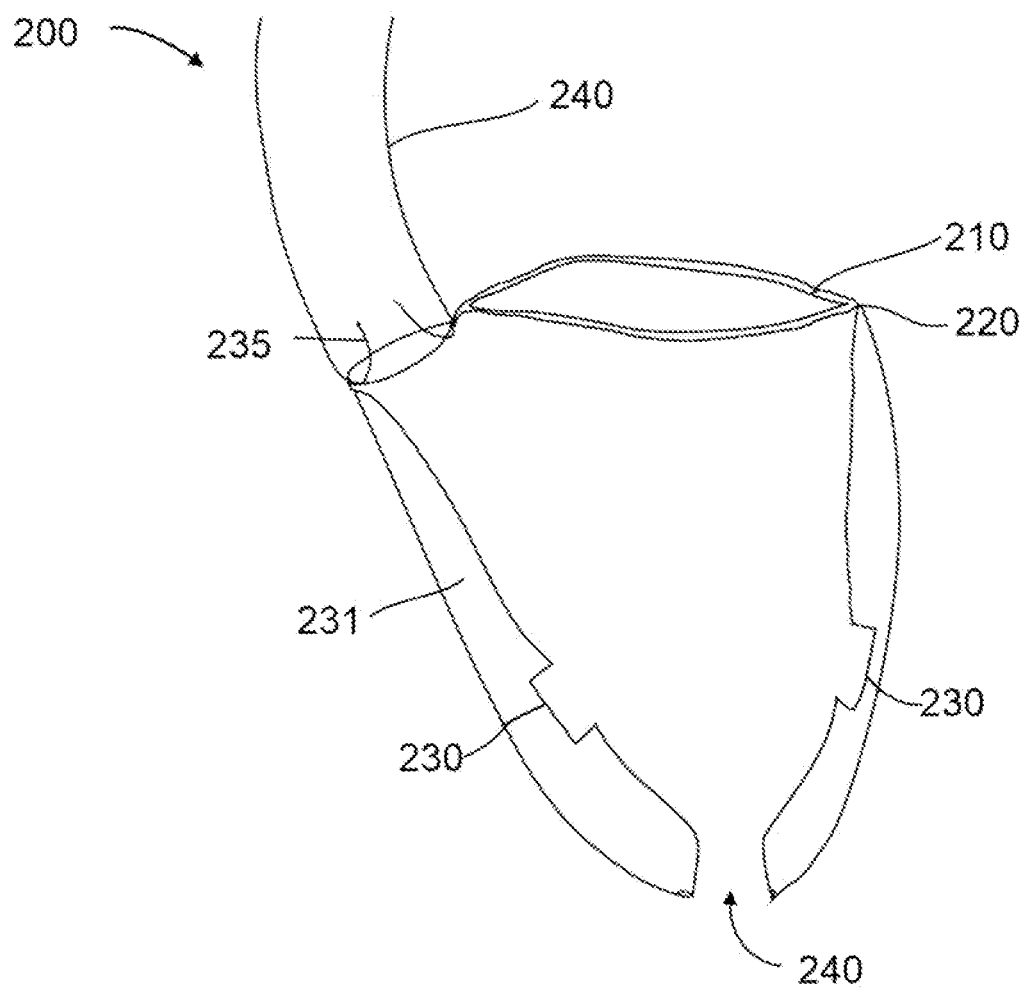
FIG. 3. illustrates an example embodiment of a 3D printed cardiac outer shell.

Referring now to FIG. 3, shown is a 3D printed cardiac outer shell 200 produced from an image of a subject's heart. The cardiac outer shell 200 contains a simulated mitral or tricuspid annulus 220, ventricular wall 231, and aorta/vein complex 235. The cardiac outer shell 200 al can also contain a groove 210 in the annulus 220 for insertion of the left atrium and an inlet 240 for the compression sac. In some embodiments, the cardiac outer shell 200 can also contain an indentation 230 for papillary muscle attachment.

Figure 4:
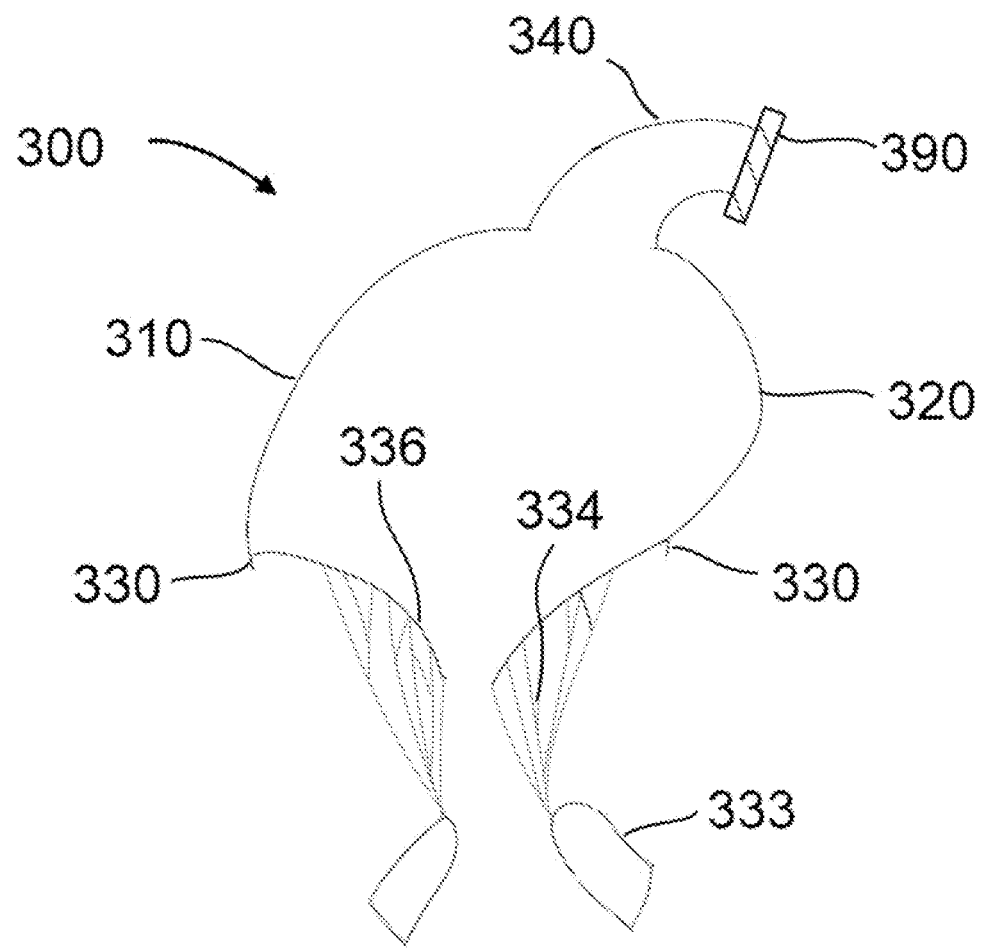
FIG. 4. illustrates an example embodiment of a 3D printed atrium and valvular apparatus.

Referring now to FIG. 4, shown is a 3D printed atrium and valvular apparatus 300 produced from an image of a subject's heart. The atrium and valvular apparatus 300 contains simulated mitral valve 336, atrial wall 310, chordae tendinae 334, aorta/vein complex 340, and papillary muscles 333. The aorta/vein complex 340 can terminate in an adaptor 390. The atrium and valvular apparatus 300 can also contain a tongue 330 for insertion of the valvular apparatus 300 into the annulus groove of the 3D printed ventricle.

Figure 5:
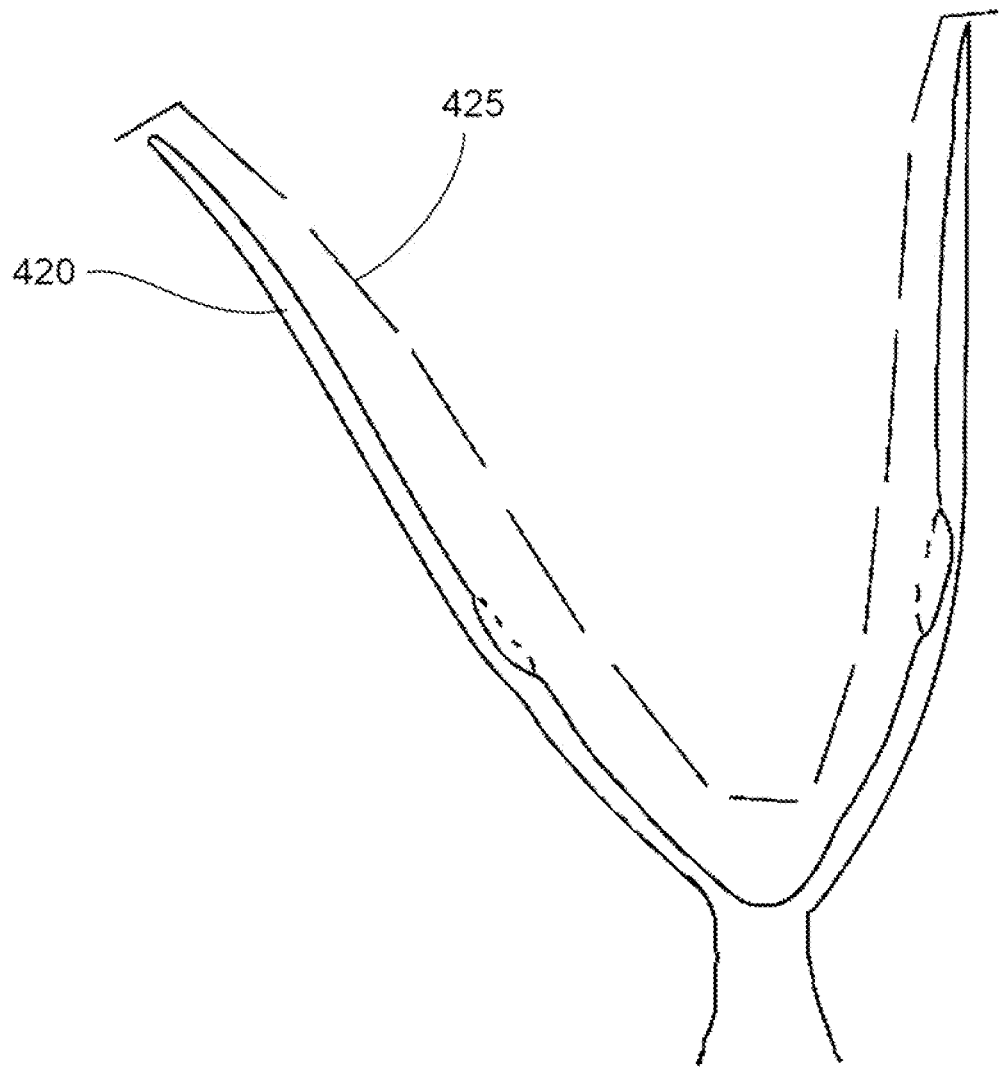
FIG. 5 illustrates an example embodiment of a compression sac and systolic delimiting cage.

Referring now to FIG. 5, shown is a compression sac 420 and systolic delimiting cage 425.

In some embodiments, the compression sac has a hardness of 10 to 50 A Shore. In some embodiments, the systolic delimiting cage has a hardness of 80 to 100 A Shore.

In some embodiments, the adapters are used to attach a closed loop of tubing to the anatomical model. In some embodiments, simulated blood is added to the closed loop of tubing.

The disclosed 3D printed heart model can be produced using standard 3D printing technologies and materials available in the art. In some embodiments, the 3D printer is a polyjet multimaterial printer. For some aspects, a resin printer may also be used. In some aspects, a mold is created and parts, such as the compression sac, are cast instead of printed.

The creation of a patient-specific 3D model begins with clinical imaging. An imaging dataset must be volumetric. Therefore, in some embodiments, the clinical imaging used to image the subject's heart is electrocardiography-gated computer tomography (CT), volumetric 3D echocardiography, or cardiac magnetic resonance (CMR). Volumetric 3D echocardiography is an attractive data source because it is abundantly available, relatively low-cost, and lacks ionizing radiation. For models of clearly imaged cardiac structures, such as ventricular chambers and valve leaflets, a 3D transesophageal echocardiography (TEE) data source may be sufficient to create a 3D patient-specific model. CT imaging can provide submillimeter tissue resolution, can clearly identify bone and pathologic calcium deposition, and is a commonly acquired imaging method before surgical or other structural interventions. In addition to excellent spatial resolution, CT is able to image patients with pacemakers, pacemaker wires, and metal implants that are not compatible with CMR scanning. In contrast, CMR can acquire high-resolution images without ionizing radiation and distinguish tissue composition without iodinated contrast media. In some embodiments, therefore, the imaging examinations comprise cardiac CT angiography, magnetic resonance imaging, or echocardiography.

Image segmentation is the process of converting the 3D anatomical information, e.g. obtained by CT, CMR, or 3D echocardiography volumetric imaging datasets, into a 3D patient-specific digital model of the target anatomic structures.

Segmentation involves several steps. Prior to segmentation, the acquired imaging dataset can be exported into a Digital Imaging and Communication in Medicine (DICOM) format (3D TEE images are converted into Cartesian DICOM format). From the DICOM dataset, the target anatomic geometry can be identified and segmented on the basis of the threshold intensity of pixels in the greyscale 2-dimensional (2D) image projections (axial, sagittal, and coronal). Segmentation masks can be created such that pixels with the same intensity range are grouped and assigned to be printed using a single material. Segmentation masks can be converted into 3D digital models using rendering techniques, and these patient-specific 3D digital models can be saved as a stereolithography file. This 3D digital model may be further modified within computer-aided design (CAD) software, where adjustments can be made to reflect the purpose of the 3D-printed model (e.g., color coding a region of interest, texturing blended materials, or adding coupling components for evaluation of the 3D-printed model within a flow loop). In general, the spatial resolution afforded by TEE is adequate for many 3D modeling purposes; however, the anatomic resolution can be further improved by combining ultrasound datasets acquired from different imaging perspectives. For example, a deep transgastric TEE image window of the mitral valve (MV) apparatus including the papillary muscles can be digitally combined with data from a mid-esophageal view of the mitral leaflets to create a more complete dataset of the entire MV complex. In addition, segmentation can be enhanced by the digital co-registration of DICOM data from complementary imaging modalities (e.g., TEE visualization of the chordae tendineae combined with CT delineation of the mitral annular calcification). The co-registration is on the basis of discreet anatomy or patho-anatomy that is present in both DICOM datasets, such as focal calcification or prosthetic material. In short, the segmentation step describes the identification of the region of interest, and may include the addition of anatomic data from more than 1 imaging source. When segmentation is complete, the final digital model can be saved as a stereolithography file, e.g. within a CAD-based software and exported for 3D printing.

There are several commercial software packages, as well as open-source freeware platforms, that can be used for the patient-specific image segmentation. The desired features of the model and the type of clinical imaging data used will generally dictate the choice of segmentation software.

The disclosed models can be printed using any suitable multi-material 3D printer. In some embodiments, the 3D printer is an additive manufacturing 3D printer. 3D printers can use images from the STL files to reconstruct three-dimensional physical models by adding material layers. Several available technologies for this three-dimensional prototyping, as well as diverse materials like polymers or plastic films can be used for the final printing of the physical model. Among the available 3D printing technologies, the PolyJet technology is commonly used to fabricate patient-specific models because they allow for the replication of very complex anatomical structures by combining multiple colors and materials simultaneously. PolyJet machines (J750 Digital Anatomy, Objet 500 Connex 3, Stratasys) print 3D objects by adding high-resolution layers (down to 16 microns resolution) and the selection of materials to approximate specific tissue properties, ranging from very soft (GelMatrix) to hard (VeroPlus) materials. In some embodiments, the tissues have an elastic modulus from the softest at $0.262$ $N/m^2$ to the hardest of $3,000,000,000$ $N/m^2$. For example, in some embodiments cardiac tissues can have an elastic modulus from $0.262$ $N/m^2$ to $0.536$ $N/m^2$. In some embodiments internal membrane material properties can have an elastic modules from $0.262$ $N/m^2$ to $1$ $N/m^2$.

A material property type that can be used to determine and select appropriate 3D printing materials can be the modulus of elasticity. The modulus of elasticity is highest for the synthetic tissue type corresponding to supportive connective tissue, lower for synthetic tissue type corresponding to dense connective tissue, lower for synthetic tissue type corresponding to loose connective/muscle tissue, and lowest for synthetic tissue type corresponding to cellular tissue.

A material property type that can be used to determine and select appropriate 3D printing materials can also be the shear modulus. The shear modulus is highest for the synthetic tissue type corresponding to supportive connective tissue, lower for synthetic tissue type corresponding to dense connective tissue, lower for synthetic tissue type corresponding to loose connective/muscle tissue, and lowest for synthetic tissue type corresponding to cellular tissue.

A material property type that can be used to determine and select appropriate 3D printing materials can be the tensile or flexural strength. The tensile or flexural strength is highest for the synthetic tissue type corresponding to supportive connective tissue, lower for synthetic tissue type corresponding to dense connective tissue, lower for synthetic tissue type corresponding to loose connective/muscle tissue, and lowest for synthetic tissue type corresponding to cellular tissue.

In some embodiments, the 3D printing materials can include rigid material elastic materials, and support materials. For example, the rigid printing materials can include at least one selected from the group consisting of VeroWhitePlus™ (RGD835), VeroWhite™, VeroBlackPlus™ (RGD875) VeroBlack™, VeroBlue™ (RGD840), High Temperature (RGD525™), VeroClear™ (RGD810), RGD720™, DurusWhite™ (RGD430), VeroGray™ (RGD850). The elastic printing materials can include at least one selected from the group consisting of TangoPlus™ (FLX 930), TangoBlack™ (FLX973), TangoBlackPlus™ (FLX980), TangoGray™ (FLX 950), TissueMatrix (MED310) and BoneMatrix (RDG516). The support material can include Soluble Support Material 706™ and GelMatrix (FLG110). (Objet Geometries/Stratasys, Rehovot Israel) Other 3D printing materials now known or developed in the future can be used.

The use of material blends can also be used for accurate representation of abnormal features within heart valves, such as the calcific structures within the aortic valve and MV, or to replicate a complex of anatomical elements with different tissue characteristics. For example, in some embodiments, portions of the inner membrane have modified properties to reflect a defect in the subject's heart, such as a myocardial infarction. In some embodiments, the modification is a decrease in the elasticity of the material. In some embodiments, potential materials can blend different levels of cardiac muscle stiffness as well as the most rigid of materials representing calcifications.

3D-printed patient-specific models can be created for a number of different applications including creation of anatomic teaching tools, development of functional models to investigate intracardiac flow, and creation of deformable blended-material models for complex procedural planning, and increasingly, patient-specific models are being deployed to assist efforts to create or refine intra-cardiac devices.

Patient-specific 3D models of aortic valve dysfunction can be readily created by combining the technologies of high-spatial resolution CT, CAD software, and multimaterial 3D printing. Aortic valve dysfunction is a spectrum of conditions that have recently been replicated using 3D printing and coupled to a flow phantom. Because severe aortic valve stenosis (AS) represents a relatively static valve configuration, a CT dataset can acquire the patient-specific anatomic detail of the aortic root, including the valve orifice area and regional calcium deposition. Such patient-specific functional models may provide a controlled and reproducible testing environment with quantitation of flow under pre-specified conditions, with potential applications including the examination of low-flow, low-gradient AS conditions, or the validation of 4-dimensional cardiac CMR methods to quantify transvalvular flow volume.

Patient-specific modeling of the aortic valve in diastole can also be used to replicate aortic valve regurgitation and compared with clinical Doppler measures of aortic regurgitation severity replicated in vitro. Patient-specific models of the aortic valve and aortic root complex can be used for performance of in vitro or bench-top transcatheter aortic valve implantation (TAVR). These constructs allow for exploration of the patient-specific features that influence the performance of transcatheter-deployed prosthetic heart valves. Such models may be especially useful for evaluating clinically challenging situations, such as the noninvasive quantification of paravalvular regurgitation severity under controlled flow conditions or for the planned deployment of endovascular stents.

In addition to functional valve replication, the modeling of the coronary artery bed can be used for several different applications. 3D printing of coronary structures can enable visualization of stenotic regions, which may serve as a bench top tool to prepare and/or practice interventional procedures within a pulsatile flow loop environment. The coronary artery tree can be clearly defined by gated-CT methods, and when 3D printed in the diastolic phase, these models can be coupled to a flow loop to replicate epicardial coronary perfusion. Such models can provide a reference standard for testing of novel diagnostic measures (e.g., CT-derived fractional flow reserve, FFR) against a controlled, in vitro, forward-flow gold standard.

Furthermore, when models are printed from optically transparent materials, techniques such as particle image velocimetry allow for direct visualization of complex flow dynamics. In addition to flow studies, these functional models can be used to simulate interventional procedures.

Congenital cardiovascular diseases are often associated with complex and unique geometry that can be very difficult to fully appreciate from 2D CT, CMR, or echocardiographic images. As such, 3D-printed modeling may play a key role to provide a more comprehensive understanding and functional evaluation of various congenital heart conditions. 3D-printed congenital heart models can be used for interventional pre-operative planning and simulations, enhanced structural orientation, functional, patient-specific hemodynamic evaluations, and testing of novel procedural pathways. A broad range of complex congenital heart anatomies can be reconstructed and 3D printed to enhance surgical planning, including the double-outlet right ventricle, atrial septal defect (ASD) and ventricular septal defect, tetralogy of Fallot as well as hypoplastic left heart syndrome. Moreover, 3D-printed models may assist with the accuracy of ventricular assist device cannula placement in patients with congenital heart disease.

In addition to the advanced imaging used for characterization of intracardiac neoplasm (e.g., echocardiography, CMR, and CT), patient-specific 3D-printed models can be used in the pre-operative and intraoperative surgical management of cardiac tumor excisions. Because cardiac tumors may extend into myocardial walls or valve structures, their radical and complete resection is rarely possible. Knowledge gained by 3D-printed modeling can positively influence the surgical strategy for intracardiac tumor management, e.g. by depicting tumor interaction with surrounding tissue in ways that difficult to appreciate using 2D or 3D imaging displays alone. 3D models that replicate specific static anatomy can therefore be used to replicate both the form and function of select cardiovascular conditions.

Patient-specific MV models with leaflets have generally been 3D printed from only rigid materials, for the purpose of replicating static leaflet and annular geometry. However, patient-specific functional models of the MV can also be printed with deformable leaflets. Clinically, the ability to predict intraprocedural challenges (i.e., difficulty in grasping mitral leaflets) has been hampered by a lack of patient-specific MV models. 3D anatomic modeling may provide a solution to determine the "best-fit" amongst the possible catheter-based therapies available.

In addition, such modeling may be valuable for predicting, and potentially avoiding, significant complications such as paravalvular regurgitation and device failure due to local calcification, or even the potentially devastating complication of left ventricular outflow tract (LVOT) obstruction by the device or displaced native valve tissue. Fused-material 3D modeling can be invaluable for pre-procedural device selection when there are patient-specific concerns about valvular calcification and its effect on the device-landing zone on either surface of MV leaflets. As catheter-based structural heart interventions become increasingly complex, the ability to effectively model patient-specific geometry, as well as the interaction of an implanted device within that geometry, will become even more valuable.

The ability to test new or revised structural heart repair devices within a range of cardiac pathologies is particularly appealing. Although other modeling options have been relied upon for many years, device development using cadaveric models cannot be used for specific-patient procedure planning. Likewise, animal models invariably lack either the correct size or the pathological element (e.g., calcification) of human cardiovascular conditions. The ability to review a clinical cohort of patients with a specific treatment target (e.g., severe degenerative mitral regurgitation with prohibitive surgical risk), perform volumetric clinical imaging, and convert that digital data into a focused 3D model of blended material properties is currently available. An example of this application is the delivery of transcatheter mitral valve (TMVR) replacement devices.

Unlike TAVR or MitraClip technologies, the development of TMVR devices and delivery techniques has been slower and more challenging. Specific anatomic considerations are fundamental for the successful implementation of such devices; yet, the principle anatomic features can vary significantly between prospective patients. The mitral annular area, anterior mitral leaflet length, aortic-mitral angle, LVOT area, and specific subvalvular and annular calcium depositions are just some of the considerations. Although many of these anatomic features can now be clearly delineated and evaluated with increasingly sophisticated 3D visualization software (e.g., 3mensio [Pie Medical Imaging BV, AJ Maastricht, the Netherlands]), in general, such tools fail to provide insight about how the device will deform or alter the native anatomy in a physical model (or within the patient). Therefore, the creation of an anatomically accurate, yet deformable patient-specific 3D model has all of the attributes of a detailed digital model, but also provides for benchtop evaluation of the deformation of the critical anatomic relations influenced by the implanted TMVR device (e.g., the magnitude of anterior leaflet displacement into the LVOT) (Central Illustration). In fact, if 3D patient-specific models are created with material properties representing diseased human tissue, then 2 central features of a structural intervention may be assessed a priori: 1) the effect of the device on anatomic configuration of native structures; and 2) the effect of native structures (especially calcium) on the deployed configuration of the implanted device (e.g., failed expansion of a TAVR device within a heavily calcified aortic root).

A pulsatile flow pump has the purpose of reproducing the heart beats. It consists of electric motor, regulator, and water reservoir, as well as electrical and hydraulic connections. It is connected to the printed heart model via connectors and/or hoses.

A number of embodiments of the invention have been described. Nevertheless, it will be understood that various modifications may be made without departing from the spirit and scope of the invention. Accordingly, other embodiments are within the scope of the following claims.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

What is claimed is:

1. A method of making a three-dimensional anatomical model of a subject's heart with simulated cardiac stroke volumes comprising:
   assembling data obtained from imaging examinations of the subject's heart, the data including anatomical tissue type and geometric location of anatomical tissue structures within the heart, and diastolic and systolic ventricular volume;
   assigning to each anatomical tissue type a synthetic tissue type corresponding to the anatomical tissue type, each synthetic tissue type having a corresponding material property type;
   creating a 3D build file containing the geometric location and material property type information for the anatomical tissue structures within the heart, wherein the anatomical tissue structures include ventricular wall, atrium, the neo-ventricular lumen, papillary muscles, and chordae tendinea;
   printing an anatomical model with 3D printing materials according to the 3D build file;
   designing and positioning a systolic delimiting cage into the neo-ventricular lumen of the printed anatomical model; and
   designing and positioning an elastic compression sac between the systolic delimiting cage and the ventricular wall of the printed anatomical model,
   wherein the elastic compression sac is in fluid communication with a pulsatile pump and wherein the systolic delimiting cage defines a boundary for inflation of the elastic compression sac corresponding to the systolic ventricular volume.

2. The method of claim 1, wherein the anatomical model is printed as a separate cardiac outer shell and atrial wall/valvular apparatus that are assembled to form the anatomical model.

3. The method of claim 2, wherein the ventricular wall has an indentation for insertion of the papillary muscle during assembly.

4. The method of claim 2, wherein the systolic delimiting cage is attached to the cardiac outer shell by a tongue and groove configuration and/or adhesives.

5. The method of claim 2, wherein the cardiac outer shell has an atrial anulus groove, and wherein the atrial wall/valvular apparatus has a tongue for insertion into the atrial anulus groove.

6. The method of claim 1, wherein the imaging examinations comprise cardiac CT angiography, magnetic resonance imaging, or echocardiography.

7. The method of claim 1, wherein the anatomical model is modified after printing to form an inlet at the apex for fluid connection of the compression sac to the pulsatile pump.

8. The method of claim 1, wherein the compression sac is printed with a 3D printer.

9. The method of claim 1, wherein the compression sac is cast in a mold.

10. The method of claim 1, wherein the compression sac has a hardness of 10 to 50 A Shore.

11. The method of claim 1, wherein the compression sac is an indented sac having the shape of the apical side of the ventricular wall with an opening at the apex for fluid connection to the pulsatile pump.

12. The method of claim 1, wherein the compression sac wraps around the papillary muscles.

13. The method of claim 1, wherein the systolic delimiting cage is 3D printed.

14. The method of claim 1, wherein the systolic delimiting cage is 3D printed as a net or cage conforming to a surface of a ventricle in systole.

15. The method of claim 1, wherein the systolic delimiting cage has a hardness of 80 to 100 A Shore.

16. The method of claim 1, further comprising adapters to attach a closed loop of tubing to the anatomical model.

17. The method of claim 16, further comprising simulated blood in the closed loop of tubing.

18. A system for simulating a subject's heart with simulated cardiac stroke volumes comprising:
- a computer to:
  - receive data obtained from imaging examinations of the patient's heart, wherein the data comprises anatomical tissue type and geometric location of anatomical tissue structures within the heart, and diastolic and systolic ventricular volume,
  - process the data to create a three-dimensional model of the patient's heart with an elastic inner membrane attached at fixation points to the anatomical tissue structures to define an outer compression sac between the inner membrane and a ventricular wall of the heart and an inner neo-ventricular lumen in fluid communication with an atrium, and
  - convert the data in a suitable format for printing by a 3D printer;
- a 3D printer that receives the three-dimensional model in the suitable format and prints a printed model of the patient's heart including the compression sac; and
- a pulsed flow pump configured for connection to the printed model by means of connectors in fluid communication with the compression sac.

* * * * *